(12) United States Patent
Katsuda et al.

(10) Patent No.: US 6,929,476 B2
(45) Date of Patent: Aug. 16, 2005

(54) DENTAL APPARATUS

(75) Inventors: Naoki Katsuda, Kyoto (JP); Kazunari Matoba, Kyoto (JP); Teruji Nakai, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 226 days.

(21) Appl. No.: 10/134,218

(22) Filed: Apr. 29, 2002

(65) Prior Publication Data

US 2002/0182564 A1 Dec. 5, 2002

(30) Foreign Application Priority Data

May 2, 2001 (JP) ........................................ 2001-135129
Apr. 26, 2002 (JP) ........................................ 2002-126446

(51) Int. Cl.⁷ .............................. A61C 3/00; A61C 1/02
(52) U.S. Cl. .............................. 433/98; 433/27; 433/99; 433/118; 433/224
(58) Field of Search ............................ 433/98, 99, 102, 433/118, 224

(56) References Cited

U.S. PATENT DOCUMENTS 5,538,423 A    7/1996  Coss et al. ..................... 433/27
5,568,028 A  * 10/1996  Uchiyama et al. .......... 318/566
5,725,533 A  *  3/1998  Carlsson ...................... 606/101
5,746,596 A  *  5/1998  Gallant et al. ................ 433/88
5,980,248 A  * 11/1999  Kusakabe et al. ............ 433/27

FOREIGN PATENT DOCUMENTS

| DE | 197 29 178 | 1/1999 |
| EP | 0 392 518 | 10/1990 |
| EP | 0 993 808 | 4/2000 |
| JP | H5-192356 | 8/1993 |
| JP | H8-000640 | 1/1996 |
| JP | H9-038108 | 2/1997 |
| JP | 9-038108 | 2/1997 |
| JP | 9-248311 | 9/1997 |
| JP | 10-026541 | 1/1998 |
| JP | 11-005457 | 1/1999 |
| JP | 11-245686 | 9/1999 |
| WO | WO 01/03601 | 1/2001 |

* cited by examiner

Primary Examiner—John J Wilson
(74) Attorney, Agent, or Firm—Koda & Androlia

(57) ABSTRACT

A dental equipment for cutting teeth, forming root canals and so on. The dental apparatus includes: an actuator for actuating a cutting tool; a load sensor for sensing a load worked in the cutting tool; and a load indicator for making an operator know the load sensed by the load sensor visually, aurally and/or tactily.

25 Claims, 9 Drawing Sheets

2 : DRIVE MOTOR
17 : TOOL

DENTAL APPARATUS

CROSS-REFERENCE TO RELATED APPLICATION

This application is based upon application Nos. 2001-135129 and 2002-126446 filed in Japan, the contents of which are hereby incorporated by reference.

BACKGROUND OF THE INVENTION

1. Field of the Invention

The present invention relates to a dental apparatus. More particularly, it relates to the dental apparatus capable of cutting teeth, forming root canals and applying to dental implant, for example, by driving a cutting tool.

2. Description of the Related Arts

Conventionally, a dental apparatus wherein the rotation of its cutting tool (file) is controlled depending on the load torque applied to the cutting tool to prevent the breakage of the cutting tool when expanding a root canal, for example, has been proposed. In this dental apparatus, the cutting tool rotates reversibly or stops when the load torque reaches a reference torque or more (for example, Japanese Non-examined Patent Publication No. Hei 9-38108).

If a root canal is bent for example, however, the load increases spontaneously even when the operator has no intention of increasing the load, and the rotation of the cutting tool stops or reverses unexpectedly. Hence, the operator is required to carry out cutting while being fully careful so that the load torque does not reach a reference load torque. However, the smaller the load, the lower the efficiency of the cutting. On the other hand, if the load is increased so as to be nearly equal to the reference load torque, the cutting tool stops or reverses frequently, thereby lowering the efficiency of the cutting in some cases. In other words, it was impossible to carry out the cutting at an appropriate load not exceeding the reference load efficiently without worries.

Furthermore, the operator is required to carry out the cutting while simultaneously checking the measurement result of a root canal length and the torque. In the conventional dental apparatus, these values were not displayed so as to be checked simultaneously, whereby the efficiency of the cutting was low.

SUMMARY OF THE INVENTION

Accordingly, it is an object of the present invention to provide a dental apparatus capable of carrying out cutting efficiently without worries.

In order to achieve the above object, according to one aspect of the present invention, there is provided a dental apparatus comprising: a driving device for driving a cutting tool; a load detector for detecting a load applied to the cutting tool; and a load information device for informing an operator of the load detected by the load detector by means of at least one of view (sight), sound and vibration.

In the above-mentioned configuration, in the case when the driving device such as a motor rotates the cutting tool, the load detector detects a drive torque produced when the driving device rotates the cutting tool as a load. In the case when the driving device such as that used for a scaler vibrates the cutting tool in its axial direction, the load detector detects a braking force required to stop the vibration as a load. In the case of the rotation of the motor, the load may be detected directly from the cutting tool itself by using a strain gauge attached to the cutting tool.

With the above-mentioned configuration, the operator can check the load applied to the cutting tool by using the load information device, visually, aurally and/or tactily.

Hence, the operator can carry out cutting efficiently without worries.

Preferably, the dental apparatus is provided with reference load information device for informing the operator of a reference load by means of at least one of view, sound and vibration.

With the above-mentioned configuration, the operator can check the difference (margin) between the load applied to the cutting tool and the reference load, visually, aurally and/or tactily. Hence, the operator can easily make an adjustment so that an appropriate load applies to the cutting tool. This makes the dental apparatus convenient.

Further, preferably, the dental apparatus further comprises provided with a reference load setting device for setting the above-mentioned reference load.

With the above-mentioned configuration, the operator can set the reference load as desired. This makes the dental apparatus easy to use.

Preferably, the dental apparatus further comprises a control device for controlling the driving device so that the load applied to the cutting tool decreases when the load detected by the load detector exceeds the reference load.

In the above-mentioned configuration, when the detected load exceeds the reference load, the control device controls the driving device and appropriately changes its drive state, for example, stops the cutting tool, rotates the cutting tool backward, decreases the rotation speed of the cutting tool or repeat the forward and backward rotation of the cutting tool. Hence, the load applied to the cutting tool can be decreased.

With the above-mentioned configuration, the load applied to the cutting tool is prevented from exceeding the reference load, thereby preventing the breakage of the cutting tool.

Preferably, the load information device is provided with plural segments for indicating the load detected by the load detector, said segments being arranged in correspondence with a value of the load. The reference load information device selects and displays at least one of the segments of the load information device or at least one of the other segments disposed near the segments of the load information device in order to indicate the reference load in accordance with substantially the same relationship as the relationship between the position of the segments of the load information device and the load. Load indicating state in which the load information device indicates the load differs from reference load indicating state in which the reference load information device indicates the reference load.

In the above-mentioned configuration, the load displayed by the load information device and the reference load displayed by the reference load information device are based on the same standard. At this time, the displaying method for the load displayed by the load information device differs from the displaying method for the reference load information device. The two can be distinguished easily, and the inequality relationship between the two can be recognized easily. For example, the load and the reference load are displayed by flashing display dots or by changing the colors thereof.

The load information device may display the load detected by the load detector immediately or at constant intervals (for example, every second).

Preferably, the load information device displays for a constant period a maximum value of the load detected by the load detector within a predetermined period.

With the above-mentioned configuration, the load information device has a peak-hold function to prevent the display from changing frequently. For this reason, the display of the load is easy to see.

Preferably, the load information device changes load indicating state in which the load information device indicates the load detected by the load detector, when the load detected by the load detector exceeds a second reference load smaller than a first reference load.

With the above-mentioned configuration, when the load detected by the load detector exceeds the second reference load and approaches the first reference load, the load information device changes the state of displaying the load by flashing display dots or by changing the colors thereof. It is thus possible to call the attention of the operator to the display visually.

Preferably, the dental apparatus further comprises a sound alarm for giving a sound when the load detected by the load detector exceeds a second reference load smaller than a first reference load.

With the above-mentioned configuration, when the load detected by the load detector exceeds the second reference load and approaches the first reference load, the sound alarm generates a sound, such as a chime sound and a buzzer sound. It is thus possible to call the attention of the operator to the display audibly.

Preferably, the dental apparatus further comprises a rotation speed control device for controlling the driving device to gradually decrease a rotation speed of the cutting tool when the load detected by the load detector approaches a reference load.

If the rotation speed decreases after the load exceeded the reference load just as in the case of the conventional device, the load exceeding the reference load is applied to the cutting tool. In the case of the above-mentioned configuration, however, when the load approaches the reference load, the rotation speed of the cutting tool decreases, and the load applied to the cutting tool is reduced. It is thus possible to prevent a load larger than the reference load from applying to the cutting tool. Hence, it is possible to prevent the breakage of the cutting tool more securely.

Preferably, the load information device is provided with plural segments arranged in one direction in correspondence with value of the load so that the positions of displayed segments among the plural segments indicate the load detected by the load detector.

With the above-mentioned configuration, the plural segments are disposed in a line or a curve, just like a bar graph or a meter, for example. The load can be displayed intuitively in accordance with the positions of the segments that are lit.

Preferably, the dental apparatus further comprises at least one of a visual direction indicator for indicating driven direction of the cutting tool visually and of an audible direction indicator for indicating driven direction of the cutting tool audibly.

With the above-mentioned configuration, when the driving device rotates the cutting tool, and when the load of the cutting tool increases and the cutting tool reverses automatically, the operator can recognize the rotation direction of the cutting tool visually or audibly. Hence, the operator can carry out operation smoothly. Furthermore, when the driving device advances or retracts the cutting tool, the operator can also carry out operation smoothly.

The driving direction of the cutting tool may be displayed (or notified by a sound) at all times or displayed (or notified by a sound) only when the driving direction is changed. In the later case, the driving direction may be displayed (or notified by a sound) only for an appropriate period after the change of the driving direction.

Preferably, the load information device is provided with a display portion placed on a handpiece in which the driving device and the load detector are disposed.

With the above-mentioned configuration, the cutting tool driven by the driving device is provided in the handpiece. When the operator looks away from the cutting tool and looks at the display portion during cutting operation, the movement of the line of sight is limited in a short distance. Hence, the operator can easily look at the display portion. The dental apparatus can thus be easy to use.

The handpiece may be connected to the controller of the dental apparatus via a tube. Instead of this configuration, a cordless handpiece provided with the driving device, the load detector and the load information device and including a battery might also be used. In this case, the operator can hold and use the handpiece without restraint. The dental apparatus can thus be used conveniently.

Preferably, the dental apparatus further comprises a root canal length measuring device and plural segments arranged two-dimensionally in a first direction and in a second direction nearly perpendicular to the first direction. The load information device indicates the root canal length measured by the root canal length measuring device in accordance with the positions of at least one of displayed segments among the plural segments arranged in the first direction. The load information device indicates the load detected by the load detector in accordance with the width of displayed segments among the plural segments arranged in the second direction.

With the above-mentioned configuration, the root canal length measured by the root canal length measuring device and the load detected by the load detector are displayed simultaneously at one area so as to be related to each other. Hence, the operator can recognize them easily.

The cutting tool may be used as an electrode for the root canal length measurement.

Furthermore, according to another aspect of the present invention, there is provided a dental apparatus configured as described below.

The dental apparatus comprises a driving device for driving a cutting tool; a root canal length measuring device for measuring a root canal length; and a control device for controlling the driving device so that a driving force of the cutting tool changes depending on a measurement value of the root canal length measured by the root canal length measuring device.

In the above-mentioned configuration, when the driving device, such as a motor, rotates the cutting tool, the control device controls the rotation speed, rotation direction, driving torque, etc. of the cutting tool driven by the driving device. In the case when the driving device such as that used for a scaler vibrates the cutting tool, the control device controls vibration amplitude, vibration cycle, vibration waveform, vibration generating force (or braking force required to stop vibration), etc.

With the above-mentioned configuration, the cutting tool can be driven in optimum conditions depending on the position of the cutting tool in the direction of the root canal length.

The cutting tool may be used as an electrode for measuring the root canal length.

Preferably, the control device includes a rotation control device for controlling the driving device so that the rotation of the cutting tool changes depending on the measurement value of the root canal length measured by the root canal length measuring device.

With the above-mentioned configuration, cutting can be carried out while changing the rotation speed and direction of the cutting tool depending on the distance to the apex and while carefully advancing the cutting tool little by little when the cutting tool approaches the apex, for example.

Preferably, the rotation control device controls the driving device so that the rotation speed of the cutting tool changes from a reference rotation speed to a preset rotation speed depending on the measurement value of the root canal length measured by the root canal length measuring device.

With the above-mentioned configuration, cutting can be carried out efficiently at the reference rotation speed until the cutting tool approaches the apex. When the cutting tool approaches the apex, the rotation speed is changed so that cutting can be carried out carefully.

Preferably, the rotation control device controls the driving device so that the rotation speed of the cutting tool changes from a reference rotation speed at a preset reduction rate depending on the measurement value of the root canal length measured by the root canal length measuring device.

With the above-mentioned configuration, by setting the reference rotation speed, the rotation speed of the cutting tool near the apex can be set eventually. The reduction rate may change stepwise or continuously depending on the measurement value of the root canal length.

Preferably, the dental apparatus further comprises a setting device for setting the reference rotation speed and the preset rotation speed.

With the above-mentioned configuration, the driving conditions of the cutting tool can be set and changed as desired. The dental apparatus can thus be used conveniently.

Furthermore, according to still another aspect of the present invention, there is provided a dental apparatus configured as described below.

The dental apparatus comprises a driving device for rotating a cutting tool; a load torque detector for detecting a load torque applied to the cutting tool; and a control device for performing one of stooping a rotation of the cutting tool; reversing a direction of the rotation; decreasing a speed of the rotation; and repeating a forward rotation thereof and a backward rotation thereof, when the load torque detected by the load torque detector exceeds a first reference load, and for controlling the driving device to perform one of increasing the speed of the rotation; rotating the cutting tool forward; and vibrating the cutting tool by applying a predetermined force, when the load torque detected by the load torque detector reaches a second reference load smaller than the first reference load.

With the above-mentioned configuration, when the load applied to the cutting tool exceeds the first reference load, the load is decreased. When the load applied to the cutting tool is smaller than the second reference load, the load is increased. Hence, the load can be set at a value between the first and second reference loads.

Furthermore, according to still another aspect of the present invention, there is provided a dental apparatus configured as described below.

The dental apparatus comprises a driving device for driving a cutting tool; a load detector for detecting a load applied to the cutting tool; a load information device for informing an operator of the load detected by the load detector by means of at least one of view, sound and vibration; a root canal length measuring device for measuring a root canal length by using the cutting tool; and a root canal length information device for informing the operator of the root canal length detected by the root canal length measuring device by means of at least one of view, sound and vibration, wherein both of the load and the root canal length are informed by the load information device and the root canal length information device.

With the above-mentioned configuration, the operator can carry out operation while simultaneously checking the measurement result of the root canal length and the load applied to the cutting tool, visually, aurally and/or tactily. The operator can thus work efficiently.

BRIEF DESCRIPTION OF THE DRAWINGS

This and other objects and features of the present invention will become clear from the following description taken in conjunction with the preferred embodiment thereof with reference to the accompanying drawings.

DETAILED DESCRIPTION OF THE PREFERRED EMBODIMENT

Figure 1:
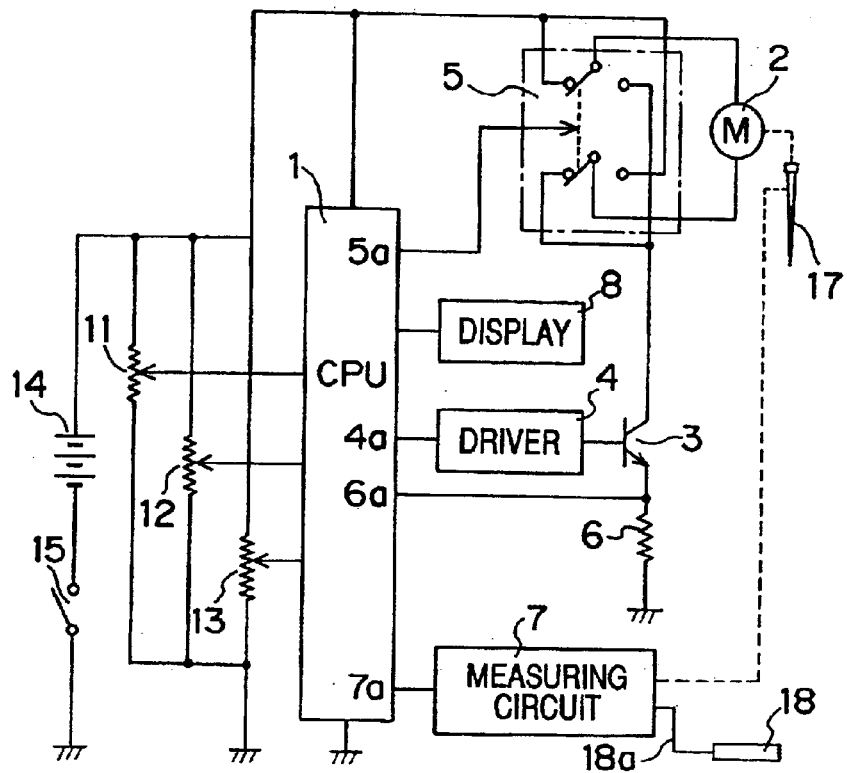
FIG. 1 is a circuit diagram of a dental apparatus in accordance with an embodiment of the present invention.

Before the description of the preferred embodiment according to the present invention proceeds, it is to be noted that like or corresponding parts are designated by like reference numerals throughout the accompanying drawings.

A dental apparatus in accordance with the embodiment of the present invention will be described below referring to FIGS. 1 to 10.

FIG. 1 is a circuit diagram of a dental apparatus in accordance with a preferred embodiment of the present invention. Reference numeral 1 designates a CPU for controlling the overall operation of the dental apparatus. Reference numeral 2 designates a motor for driving a cutting tool 17. Reference numeral 3 designates a transistor switch. Reference numeral 4 designates a driver circuit for driving the transistor switch. Reference numeral 5 designates a rotation direction selection switch. Reference numeral 6 designates a resistor for detecting a load torque. Reference numeral 7 designates a root canal length measurement circuit. Reference numeral 8 designates a display device. Reference numeral 11 designates a variable resistor for setting a reference load torque. Reference numeral 12 designates a variable resistor for setting a duty ratio. Reference numeral 13 designates a variable resistor for setting a reference position. Reference numeral 14 designates a battery. Reference numeral 15 designates a main switch. Reference numeral 17 designates the cutting tool. These are connected to the CPU 1 as shown in the figure.

The driver circuit 4 is activated by a control signal output from the terminal 4a of the CPU 1 and turns ON/OFF the transistor switch 3. The CPU 1 outputs a control signal that is a pulse signal having a constant cycle and a duty ratio depending on the setting of the variable resistor 12. The motor 2 rotates depending on the output corresponding to the duty ratio.

The CPU 1 measures the voltage at the terminal 6a of the resistor 6 to detect the load torque of the motor 2. Furthermore, the voltage at the terminal 5a of the CPU 1 is changed to Lo/Hi, whereby the rotation direction selection switch 5 is activated and the motor 2 can be rotated forward and backward. The CPU 1 detects the reference load torque, duty ratio and reference position preset by the variable resistors 11, 12 and 13.

Figure 2:
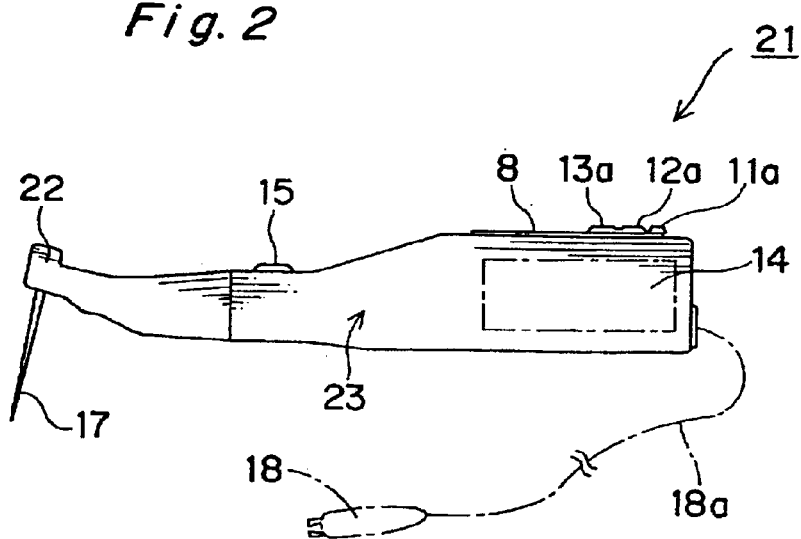
FIG. 2 is an external view showing the dental apparatus shown in FIG. 1.

FIG. 2 is an external view showing a cordless dental apparatus 21 comprising the components of the circuit shown in FIG. 1. In this embodiment, a dental handpiece 23 is shown. At the tip of the head 22 of the dental handpiece 23, a root canal forming file (hereafter referred to as the file 17) is mounted as the cutting tool 17. The file 17 is electrically connected to the measurement terminal of the root canal length measurement circuit 7 via a conductive member inside the handpiece 23 so as to be used as an electrode for root canal length measurement. A grounding electrode 18 is electrically connected to the grounding terminal of the root canal length measurement circuit 7 via a lead wire 18a. Reference numeral 11a designates a reference load torque setting device. Reference numeral 12a designates a rotation speed setting device. Reference numeral 13a designates a reference position setting device for controlling the driving device for the cutting tool depending on the output of the root canal length measurement circuit 7. In this embodiment, the reference load torque setting device 11a, the rotation speed setting device 12a and the reference position setting device 13a are mounted on the handpiece 23. However, in a configuration wherein a separate controller is connected to the handpiece 23 via a cord, the setting device 11a, 12a and 13a may be mounted on the separate controller.

Figure 3:
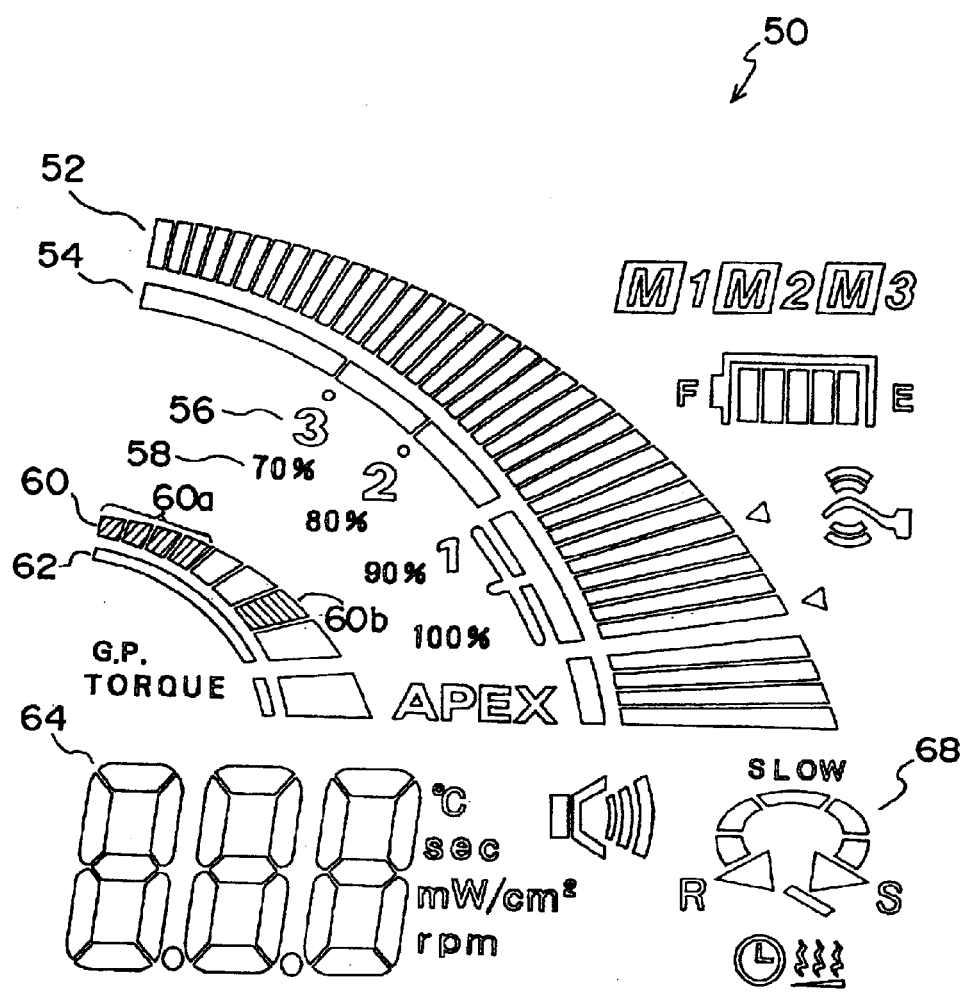
FIG. 3 is a plan view showing a LCD panel on a display portion of the dental apparatus shown in FIG. 1.

FIG. 3 shows an example of a LCD (Liquid Crystal Display) panel 50 mounted on the display device 8.

The LCD panel 50 comprises a dot display portion 52 including numerous segments for minutely displaying a measured root canal length, a zone display portion 54 for displaying the measured root canal length stepwise in divided zones, a boundary display portion 56 for displaying the boundaries of the zones and an attainment rate display portion 58 for displaying the rate of attainment to an apex. As the measured root canal length increases, the segments are lit sequentially downward.

Furthermore, the LCD panel 50 is provided with a dot display portion 60 including numerous segments for displaying a measured load torque and a zone display portion 62 for displaying the load torque stepwise in divided zones. As the measured load torque increases, the segments are lit sequentially downward.

For example, the diagonally shaded segments 60a of the dot display portion 60 are lit depending on the measured load torque. A peak-hold function is provided to prevent the display from changing frequently. In other words, the maximum of the load torque measured within a predetermined time is displayed for a constant time.

Among the segments of the dot display portion 60, a segment 60b corresponding to the reference load torque that is preset by using the variable resistor 11 is also lit. Hence, the margin between the measured load torque and the reference load torque can be recognized at a glance.

In addition, numeral 64 designates a numeric value display portion for displaying the numeric values of rotation speed and load. Reference numeral 68 designates a rotation display portion for displaying the direction of rotation and the slow/rapid distinction of rotation speed.

The measured load torque and the preset reference load torque can be displayed in various ways as described below.

Figures 4A, 4B, 4C:
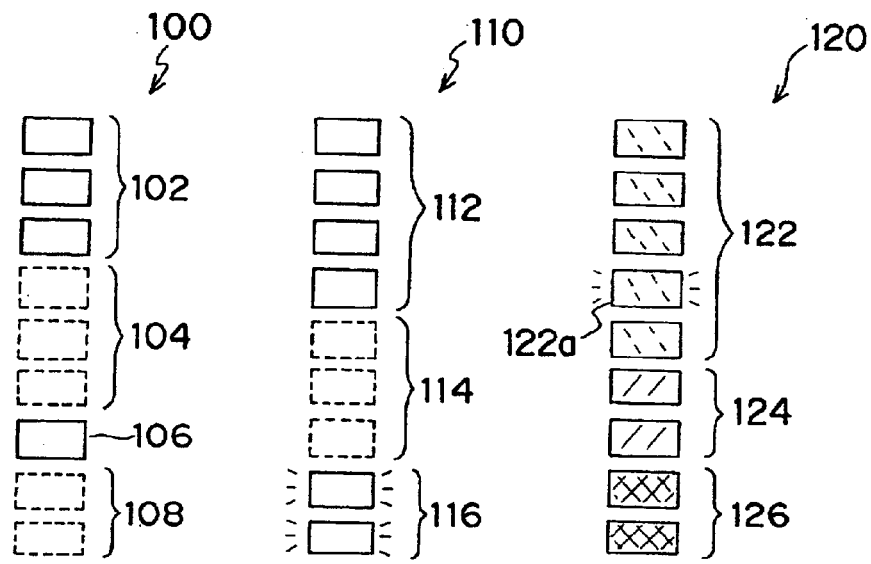
FIGS. 4A, 4B and 4C are views illustrating examples of display as displayed on the LCD panel.

Alternatively, for example, when segments arranged one-dimensionally are used, display can be carried out as shown in the schematic views of FIGS. 4A, 4B and 4C.

In an example 100 of display shown in FIG. 4A, segments 102 are lit in green sequentially downward depending on the measured load torque. A segment 106 corresponding to the preset reference load torque is lit in red. The other segments 104 and 108 are not lit.

In an example 110 of display shown in FIG. 4B, segments 112 are lit in green sequentially downward depending on the measured load torque. Segments 116 for displaying a torque larger than the preset reference load torque are lit so as to flash in red. The other segments 114 are not lit.

In an example 120 of display shown in FIG. 4C, segments are divided into three zones and lit in three colors depending on the preset reference load torque. For example, segments 122 for displaying torques sufficiently smaller than the preset reference load torque are lit in green. Segments 124 for displaying torques close to the preset reference load torque is lit in yellow. Segments 126 for displaying torques larger than the preset reference load torque are lit in red. In addition, a segment 122a corresponding to the preset reference load torque flashes.

Figure 5:
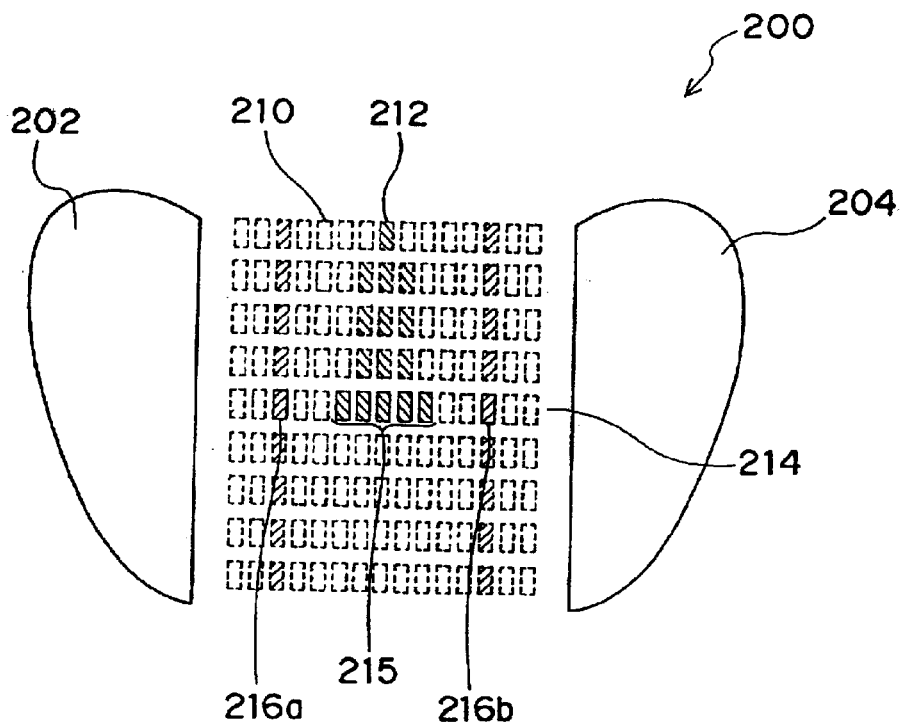
FIG. 5 is a view illustrating another example of display as displayed on the LCD panel.

FIG. 5 shows an example 200 of display wherein plural segments 210 are arranged two-dimensionally to display the result of root canal length measurement, as well as a measured load torque and the preset reference load torque.

Segments 210 are arranged in matrix on a LCD panel between display portions 202 and 204 that schematically indicate a tooth. As the formation of a root canal advances and as the length of the root canal becomes larger and the end of the root canal approaches the apex, lower segments are lit. The larger the load torque, the wider the segments horizontally arranged from each of the center column segments 212 are lit in the horizontal direction. For example, diagonally shaded segments 215 are lit in green. The vertical position of the segments 215 indicates the distance between the end of the root canal and the apex. Furthermore, the horizontal length (width) of the segments 215 corresponds to the measured load torque. In the same row as that of the segments 215, two diagonally shaded segments 216a and 216b are lit in red. From the segments 216a and 216b, segments are disposed linearly in the vertical direction. The distance between the two segments 216a and 216b indicates the preset reference load torque. The distance from the segments 215 to the segments 216a and 216b indicates a margin to the reference load torque.

In this example, the remaining distance to the apex and the difference between an actual load torque and the reference load torque are displayed on a single display area, thereby enhancing convenience.

Furthermore, in this example, the change of the load torque with respect to the root canal length is stored sequentially and displayed continuously. However, instead of storing the change sequentially and displaying it continuously, only the current root canal length and the load torque corresponding thereto may be displayed in real time. In addition, instead of the segments 216a and 216b, printed continuous solid lines may be used.

Figure 6:
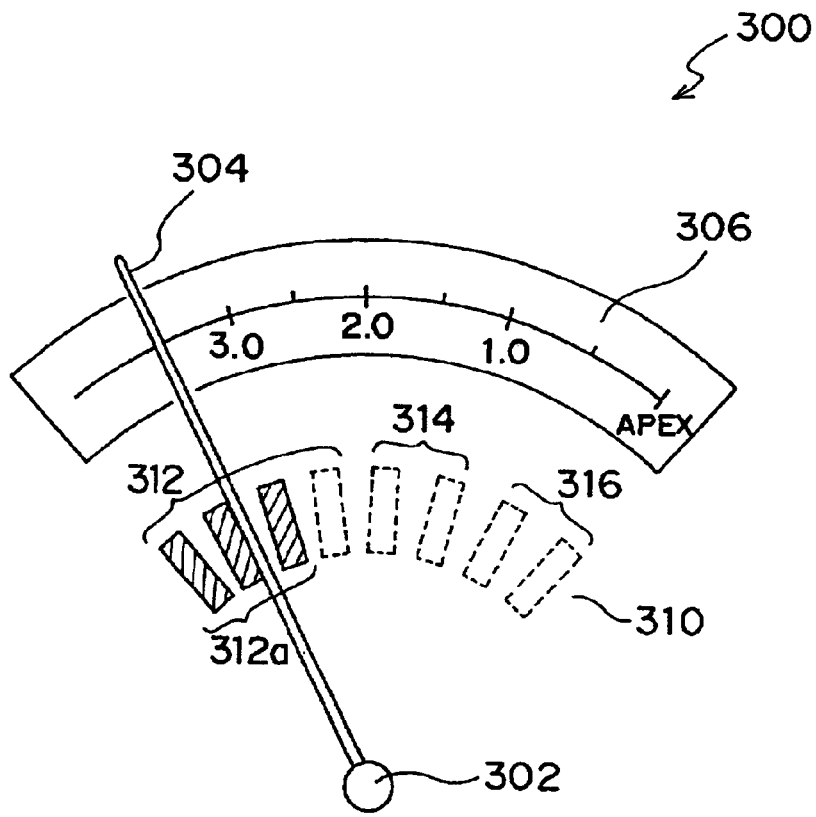
FIG. 6 is a view illustrating still another example of display as displayed on the LCD panel.

FIG. 6 shows another example 300 of display for displaying the result of root canal length measurement and load torque.

The root canal length is displayed by an analog indication needle 304 rotating around a shaft 302. Reference numeral 306 designates a scale for the indication needle 304. The load torque is displayed by segments 310 arranged below the scale 306. As the segments 310 are lit wider in a clockwise direction, a larger load value is displayed. Among the segments 310, only the segments 312a corresponding to the detected load torque are lit. The segments 310 may be divided in colors depending on the reference load torque. For example, segments 312 for displaying torques sufficiently smaller than the preset reference load torque are lit in green. Segments 314 for displaying torques close to the preset reference load torque are lit in yellow. Segments 316 for displaying torques larger than the preset reference load torque are lit in red.

Figure 7:
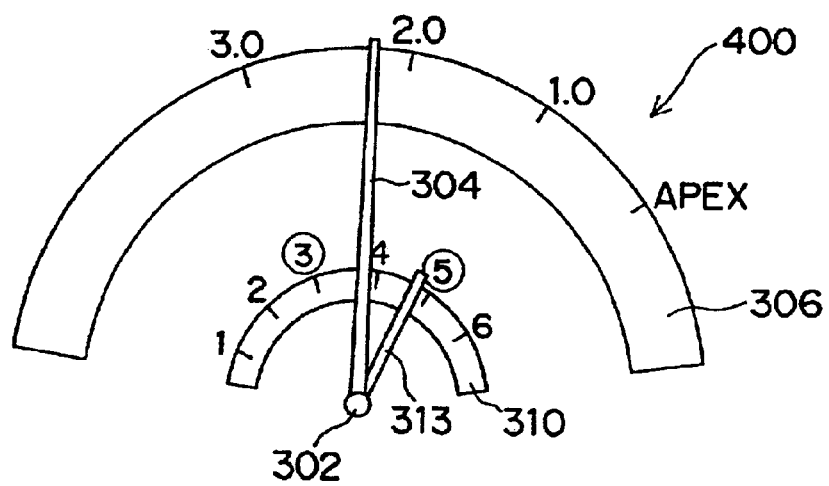
FIG. 7 is a view illustrating a further example of display as displayed on the LCD panel.

FIG. 7 shows another example 400 of display for displaying the result of root canal length measurement and the load torque. The root canal length is displayed by an analog indication needle 304 rotating around a shaft 302. Reference numeral 306 designates a scale for the indication needle 304. The load torque is displayed by a scale 310 disposed below the scale 306. As an analog indication needle 313 moves in a clockwise direction, a larger load value is displayed. The load torque obtained at a specific root canal length is displayed by the analog indication needle 313 and the scale 310. As described above, the result of the root canal length measurement and the load torque are displayed simultaneously. Hence, the operator can carry out treatment while checking situations wherein the cutting tool is approaching the apex and the torque is changing. For this reason, the root canal can be expanded smoothly without damaging the cutting tool. In addition, these two display means can be mounted on a cordless handpiece.

Next, the control of the dental apparatus 21 will be described below referring to FIGS. 8 to 10.

Figure 8:
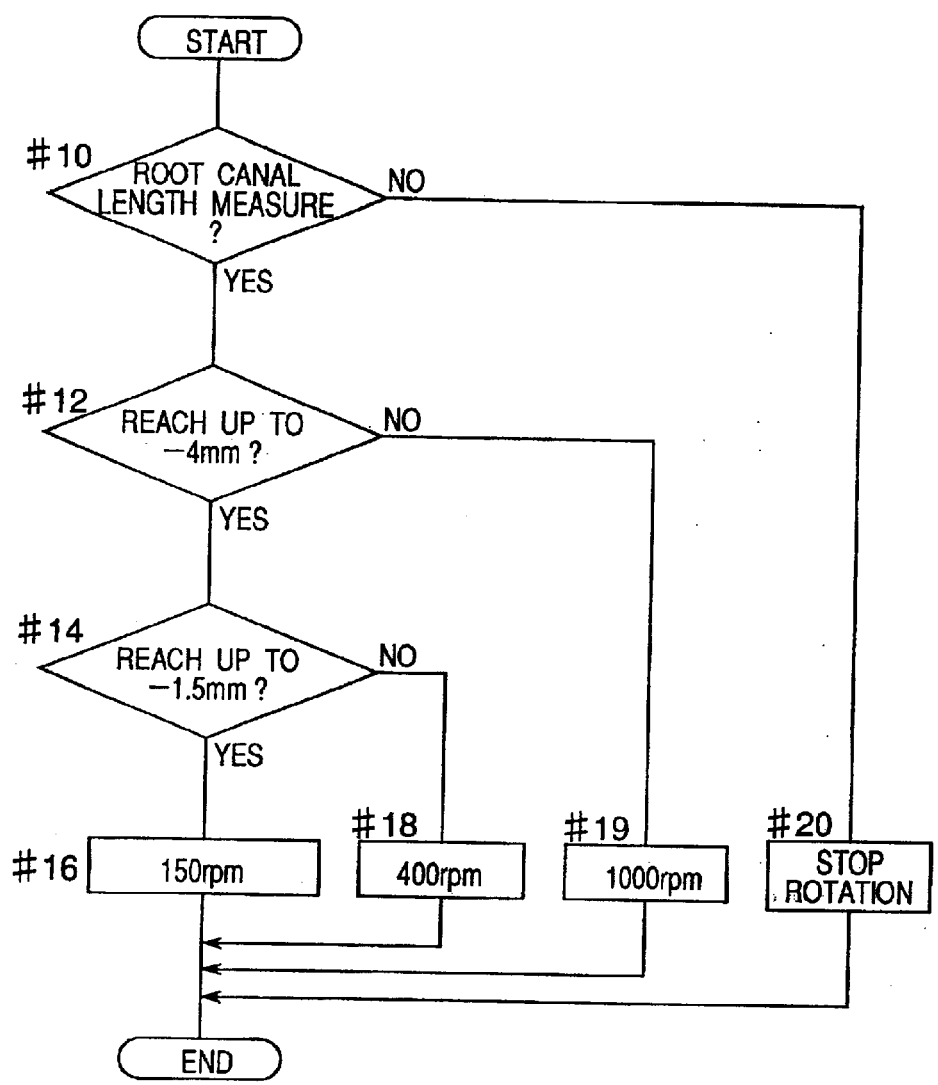
FIG. 8 is an example of a flowchart for the control of the dental apparatus.

FIG. 8 is a flowchart for the control of the dental apparatus 21 depending on the result of root canal length measurement. The CPU 1 repeatedly carries out the control flow shown in the figure at appropriate timing.

First, the CPU 1 determines whether root canal length measurement is possible or not (at step #10). When the measurement is impossible (NO at step #10), the CPU 1 stops the motor 2 (at step #20). When the measurement is possible (YES at step #10), the CPU 1 determines whether the end of the root canal has reached a position up to 4 mm to the apex or not (at step #12). Until the end of the root canal reaches the position up to 4 mm to the apex (NO at step #12), the CPU 1 drives the motor 2 so that the file 17 rotates at 1000 rpm (at step #19).

When the end of the root canal reaches the position up to 4 mm to the apex (YES at step #14), the CPU 1 determines whether the end of the root canal has reached a position up to 1.5 mm to the apex or not (at step #14). Until the end of the root canal reaches the position up to 1.5 mm to the apex (NO at step #14), the CPU 1 drives the motor 2 so that the file 17 rotates at 400 rpm (at step #18).

When the end of the root canal reaches the position up to 1.5 mm to the apex (YES at step #14), the CPU 1 drives the motor 2 so that the file 17 rotates at 150 rpm (at step #16).

By the control shown in FIG. 8, the motor speed is automatically set at the high speed so that the cutting tool can carry out efficient cutting at the upper portion of the root canal. When the end of the root canal approaches the apex, the motor speed is automatically changed to the low speed to prevent the breakage of the file 17. Hence, the operator is not required to change the setting of the rotation speed depending on the position of the end of the root canal, whereby the operation can be carried out efficiently and conveniently.

The preset distances (4 mm and 1.5 mm) up to the apex in FIG. 8 and the rotation speeds (1000 rpm, 400 rpm and 150 rpm) of the motor 2 may be changed as desired by the operator. In addition, the rotation speed of the motor 2 may be changed continuously.

Furthermore, intermediate rotation speeds may be set by multiplying the initial rotation speed (maximum speed) of the motor 2 by preset coefficients.

Figure 9:
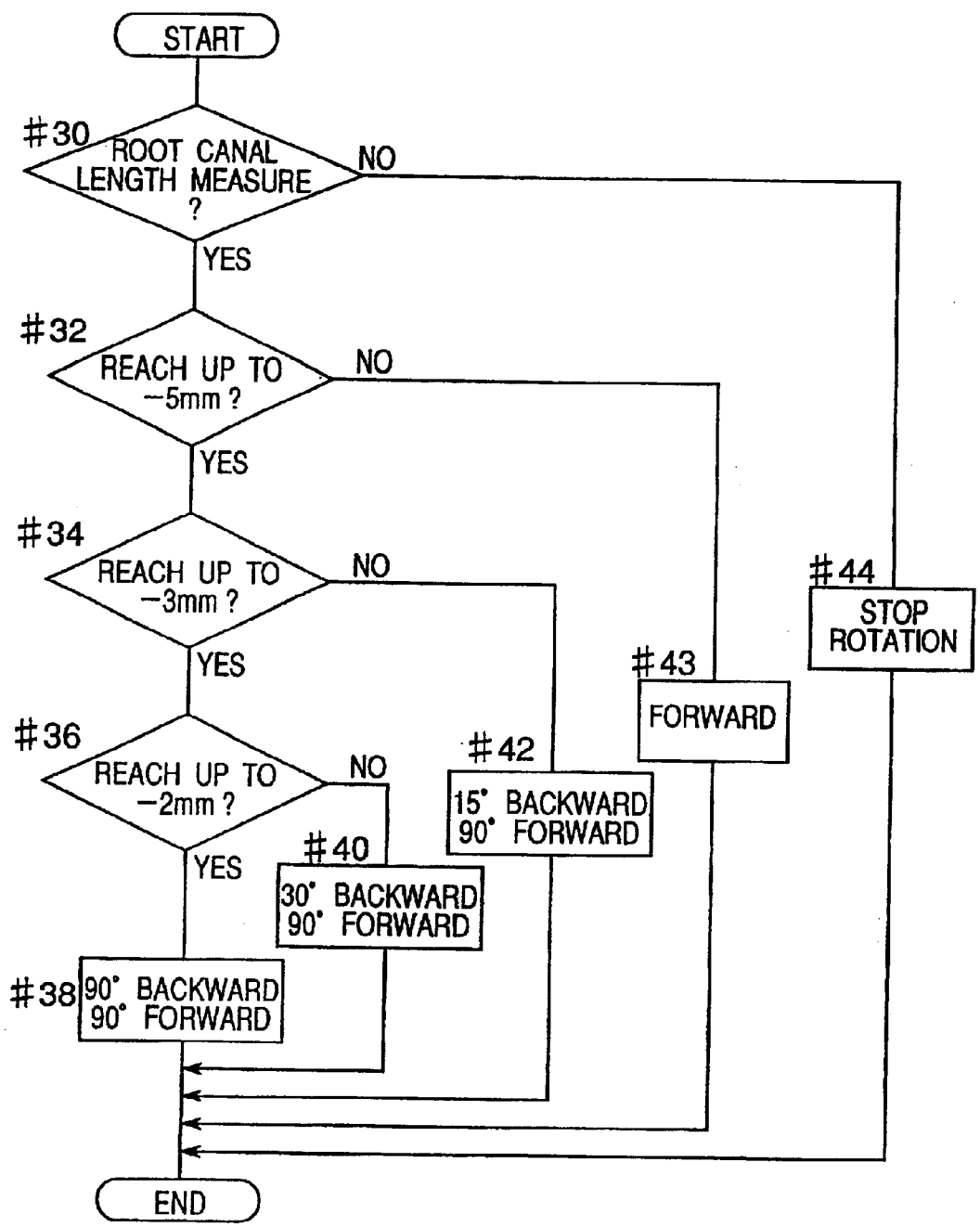
FIG. 9 is another example of a flowchart for the control of the dental apparatus.

FIG. 9 is another flowchart for the control of the dental apparatus 21 depending on the result of the root canal length measurement. The CPU 1 repeatedly carries out the control flow shown in the figure at appropriate timing.

First, the CPU 1 determines whether root canal length measurement is possible or not (at step #30). When the measurement is impossible (NO at step #30), the CPU 1 stops the motor 2 (at step #44). When the measurement is possible (YES at step #30), the CPU 1 determines whether the end of the root canal has reached a position up to 5 mm to the apex or not (at step #32). Until the end of the root canal reaches the position up to 5 mm to the apex (NO at step #32), the motor 2 rotates forward (at step #44).

When the end of the root canal reaches the position up to 5 mm to the apex (YES at step #32), the CPU 1 determines whether the end of the root canal has reached a position up to 3 mm to the apex or not (at step #34). Until the end of the root canal reaches the position up to 3 mm to the apex (NO at step #34), the motor 2 rotates 15 degrees backward and 90 degrees forward repeatedly (at step #42).

When the end of the root canal reaches the position up to 3 mm to the apex (YES at step #34), the CPU 1 determines whether the end of the root canal has reached a position up to 2 mm to the apex or not (at step #36). Until the end of the root canal reaches the position up to 2 mm to the apex (NO at step #36), the motor 2 rotates 30 degrees backward and 90 degrees forward repeatedly (at step #40).

When the end of the root canal reaches the position up to 2 mm to the apex (YES at step #36), the motor 2 rotates 90 degrees backward and 90 degrees forward repeatedly (at step #38).

By the control shown in FIG. 9, when the end of the root canal reaches the apex, the motor 2 rotates backward and forward repeatedly, whereby it is possible to prevent the breakage of the file 17.

Figure 10:
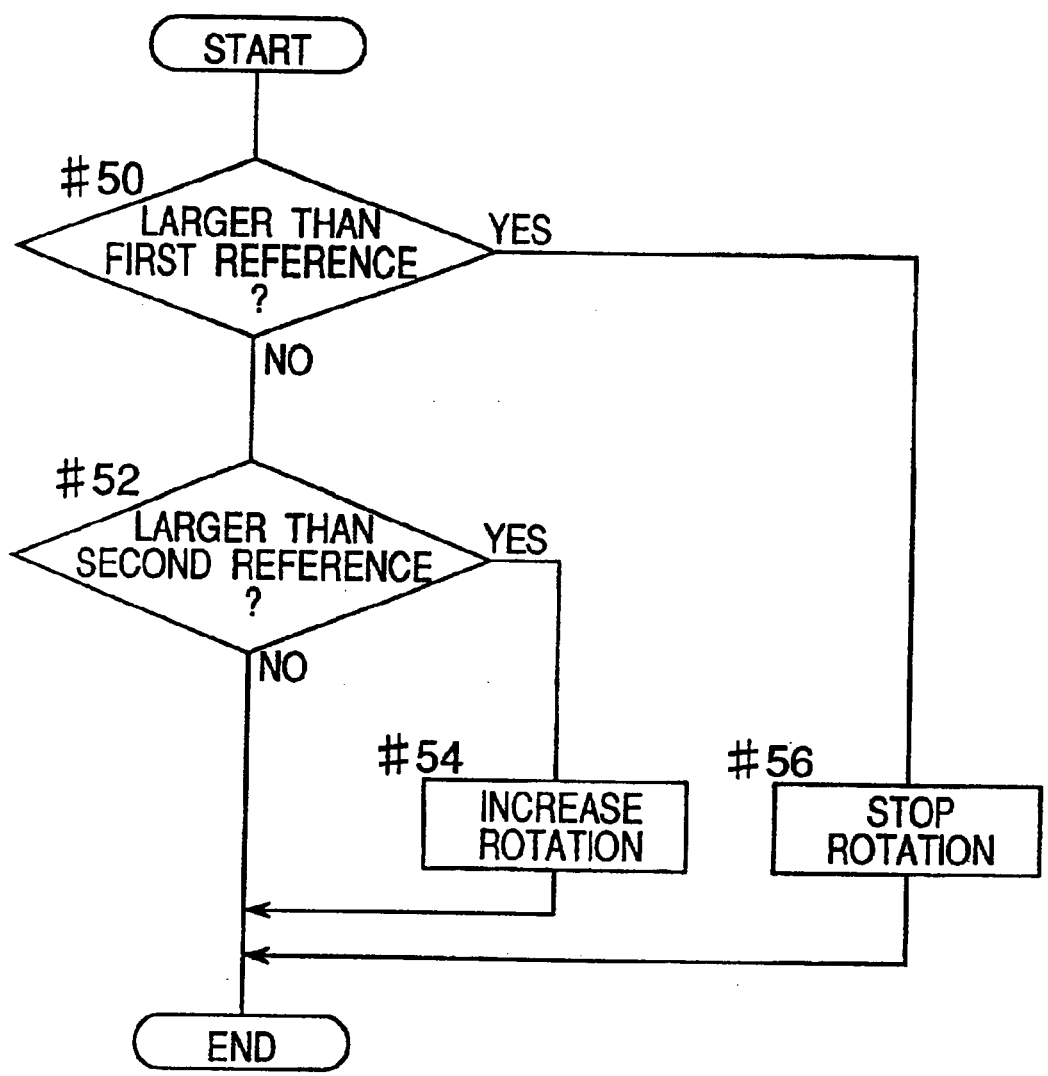
FIG. 10 is still another example of a flowchart for the control of the dental apparatus.

FIG. 10 is a flowchart for the control of the dental apparatus 21 depending on the result of load torque measurement. The CPU 1 repeatedly carries out the control flow shown in the figure at appropriate timing.

First, the CPU 1 compares the measurement value of the load torque with a preset reference load torque (referred to as "first reference" in FIG. 10)(at step #50). When the measurement value of the load torque is larger than the reference load torque (YES at step #50), the CPU 1 stops the rotation of the motor 2 (at step #56). Instead of stopping the rotation of the motor 2 at step #56, the motor 2 may be rotated backward.

When the measurement value of the load torque is not larger than the reference load torque (NO at step #50), the measurement value of the load torque is compared with a value (referred to as "second reference" in FIG. 10) that is smaller than the reference load torque by a predetermined value (at step #52). When the measurement value of the load torque is smaller than the second reference (YES at step #52), the rotation speed of the motor 2 is increased (at step #54).

Hence, the load torque is controlled so as to be set at a value between the first reference and the second reference. The cutting can thus be carried out efficiently while preventing the breakage of the file 17.

Figure 11:
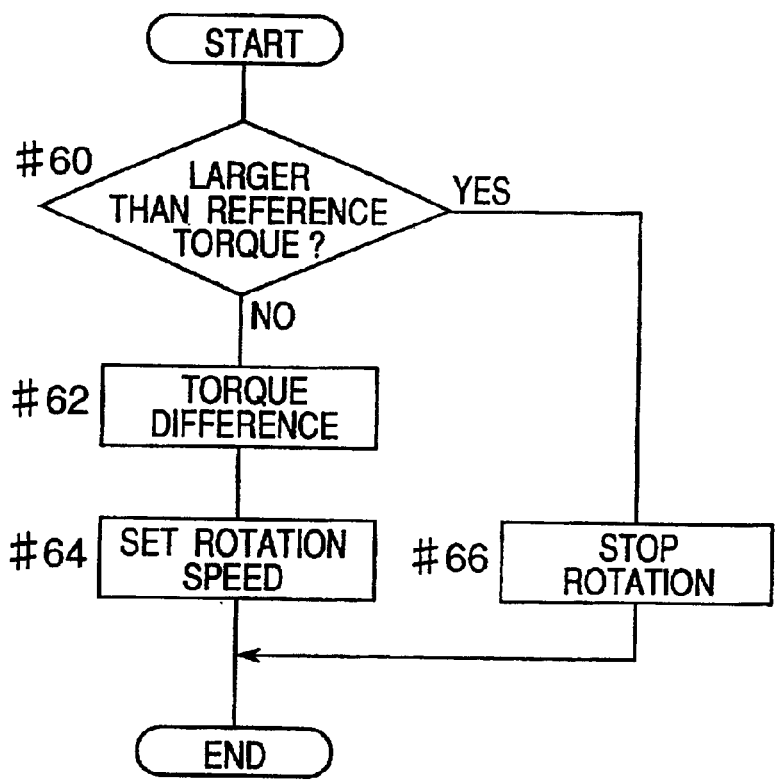
FIG. 11 is a still further example of a flowchart for the control of the dental apparatus.

FIG. 11 is another flowchart for the control of the dental apparatus 21 depending on the result of load torque measurement. The CPU 1 repeatedly carries out the control flow shown in the figure at appropriate timing.

First, the CPU 1 compares the measurement value of the load torque with a preset reference load torque (at step #60). When the measurement value of the load torque is larger than the reference load torque (YES at step #60), the CPU 1 stops the rotation of the motor 2 (at step #66). Instead of stopping the rotation of the motor 2 at step #66, the motor 2 may be rotated backward.

When the measurement value of the load torque is not larger than the reference load torque (NO at step #60), the difference (hereafter referred to as "torque difference") between the measurement value of the load torque and the reference load torque is obtained (at step #62). The motor 2 is rotated at a rotation speed proportional to the torque difference (at step #64).

In other words, the rotation speed N of the motor 2 is represented by the following equation (1).

$$N = \alpha \{N_0 \times (T_0 - T)/T_0\} \qquad (1)$$

wherein $T_0$ is the reference load torque, T is the measurement value of the load torque, N0 is the maximum speed (1000 rpm for example) of the motor 2, and $\alpha$ is a constant. Although the constant $\alpha$ is generally a fixed value, it may be varied.

Hence, as the measurement value T of the load torque approaches the preset reference load torque T0, the rotation speed N of the motor 2 decreases gradually.

As described above, the measurement result of the root canal length and the torque are displayed simultaneously during the operation of the dental apparatus. The operator can thus carry out cutting efficiently without worries while checking the displayed values.

Although the present invention has been fully described in connection with the preferred embodiment thereof with reference to the accompanying drawings, it is to be noted that various changes and modifications are also apparent to those skilled in the art.

For example, instead of using the display device 8, or combining with the display device 8, a sound alarm, which changes the sound depending on detected load and/or measured root canal length, may be used.

Figure 12:
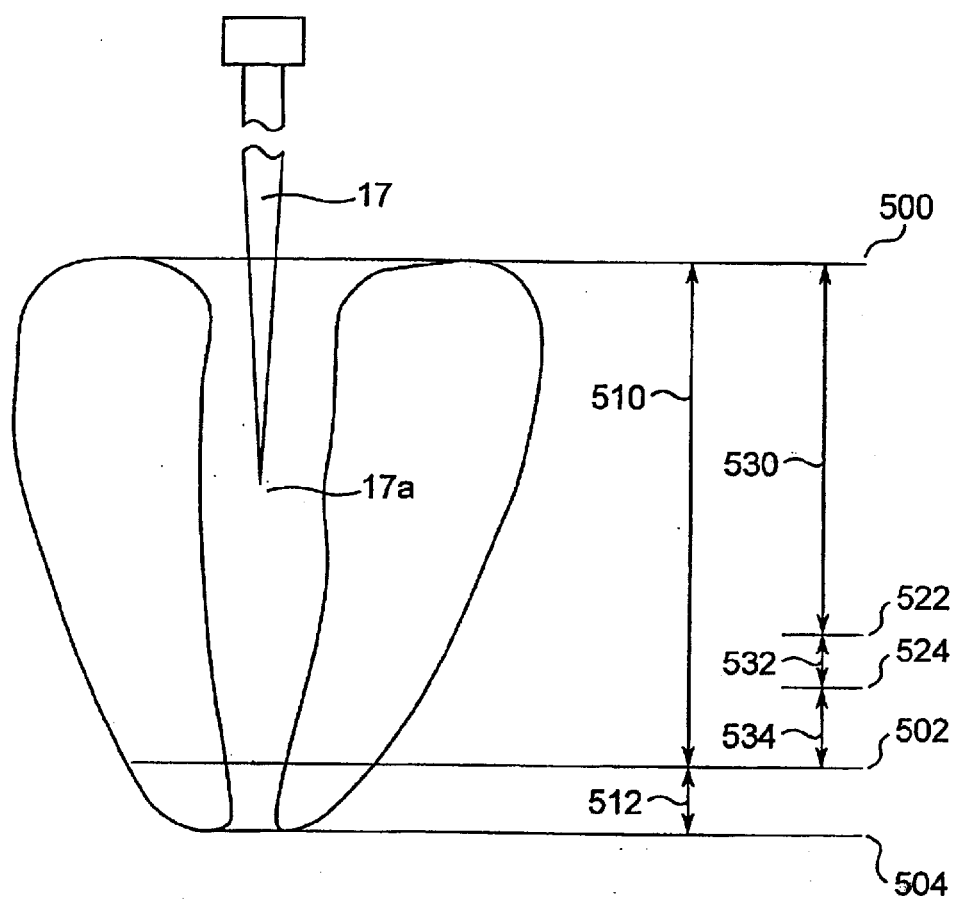
FIG. 12 is an example showing an operation of a sound alarm provided with the dental apparatus.

FIG. 12 shows an embodiment schematically. A sound alarm generates two types of sound, one of which informs an operator of the root canal length information, another of which informs the operator of the load information. Reference numeral 500 designates a crown of a tooth. Reference numeral 504 designates an apex of the tooth. Reference numeral 502 designates a reference position short of the apex 504 by a distance, which can be set and changed as desired.

As for the root canel information, one type of sound generated by the sound alarm is relatively high, until the end of the root canel reaches the reference position 502, or when the tip 17a of a cutting tool 17 is placed in a section as shown by reference numeral 510. After reaching the reference position 502, or when the tip 17a is placed in a section as shown by reference numeral 512, one type of sound becomes relatively low.

As for the load information, another type of sound generated by the sound alarm stops until detected load torque exceeds a first reference value 522, or when detected load torque is placed in a section as shown by reference numeral 530. Note that it is possible to inform an operator that detected load torque does not exceed the first reference value 522, by stopping the sound, or by silence. After detected load torque exceeds the first reference value 522 and until detected load torque exceeds a second reference value 524 smaller than the first reference value 522, or when detected load torque is placed in a section as shown by reference numeral 532, another type of sound sounds interruptedly. After detected load torque exceeds the sound reference value 524, or when detected load torque is placed in a section as shown by reference numeral 534, another type of sound sounds continuously. The first reference value 522 and the second reference value 524 can be set and changed as desired.

In addition, depending on measured root canel length and/or detected load torque, the cutting tool 17 may be driven. For example, when the end of the root canel (the tip 17a of the cutting tool 17) reaches the reference point 502, and/or when detected load torque is placed in the section 532 and/or the section 534, it is possible to be controlled so as to perform stopping the cutting tool 17, reversing the rotation thereof, decreasing a speed of the rotation thereof, or repeating forward and backward rotation thereof.

In the embodiment, the operator does not need to watch any display or indication of the apparatus in order to know the root canel information and the load information. Hence the operator can treat the tooth accurately and precisely, watching only the treated area.

Furthermore, a vibrator, which an operator can feel, may be used in order to inform the operator of the load information and/or the root canal length information, instead of using the display device 8 and/or the sound alarm, or combining therewith. Alternatively, the rotation speed of the cutting tool may be controlled according to the value of detected load torque. Specifically, when detected torque exceeds a preset value, the rotation speed of the cutting tool is not reduced to only preset speed, but to a speed related to the detected load torque. For example, when detected load torque is higher, a speed to be reduced is smaller. After detected torque does not exceed the preset value, the rotation speed of the cutting tool is controlled in the same manner as before detected torque exceeds the present value.

What is claimed is:

1. A dental apparatus comprising:
   a driving device for driving a cutting tool;
   a load detector for detecting a load applied to the cutting tool;
   a load information device for inform an operator of the load detected by the load detector by means of at least one of view, sound and vibration;
   a root canal length measuring device for measuring a root canal length by using the cutting tool; and
   a root canal length information device for informing the operator of the root canal length detected by the root canal length measuring device by means of at least one of view, sound and vibration, wherein the load and the root canal length are informed simultaneously by the load information device and the root canal length information device.

2. The dental apparatus as claimed in claim 1, further comprising a reference load information device for informing the operator of a reference load by means of at least one of view, sound and vibration.

3. The dental apparatus as claimed in claim 2, further comprising a reference load setting device for setting the reference load.

4. The dental apparatus as claimed in claim 2, further comprising a control device for controlling the driving device so that the load applied to the cutting tool decreases when the load detected by the load detector exceeds the reference load.

5. The dental apparatus as claimed in claim 4, wherein the control device controls the driving device to perform one of stopping a rotation of the cutting tool; reversing the rotation thereof; decreasing a speed of the rotation thereof; and repeating forward and backward rotations thereof, when the load detected by load detector exceeds the reference load.

6. The dental apparatus as claimed in claim 2,
   wherein the load information device is provided with plural segments for indicating the load detected by the load detector, said segments being arranged in correspondence with a value of the load,
   wherein the reference load information device selects and displays at least one of the segments of the load information device in order to indicate the reference load in accordance with substantially the same relationship as the relationship between the position of the segments of the load information device and the load, and
   wherein load indicating state in which the load information device indicates the load differs from reference load indicating state in which the reference load information device indicates the reference load.

7. The dental apparatus as claimed in claim 6, wherein the load indicating state differs from the reference load indicating state with one of flashing at least one of the segments and changing color thereof.

8. The dental apparatus as claimed in claim 2,
   wherein the load information device is provided with plural segments for indicating the load detected by the load detector, said segments being arranged in correspondence with a value of the load,
   wherein the reference load information device is provided with plural segments disposed near the segments of the load information device, in which the reference load information device selects and displays at least one of segments thereof in order to indicate the reference load in accordance with substantially the same relationship as the relationship between the position of the segments of the load information device and the load, and
   wherein load indicating state in which the load information device indicates the load differs from reference load indicating state in which the reference load information device indicates the reference load.

9. The dental apparatus as claimed in claim 8, wherein the load indicating state differs from the reference load indicating state with one of flashing at least one of the segments and changing color thereof.

10. The dental apparatus as claimed in claim 1, wherein the load information device is provided with plural segments arranged in one direction in correspondence with value of the load so that the positions of displayed segments among the plural segments indicate the load detected by the load detector.

11. The dental apparatus as claimed in claim 1, wherein the load information device displays for a constant period maximum value of the load detected by the load detector within a predetermined period.

12. The dental apparatus as claimed in claim 1, wherein the load information device changes load indicating state in which the load information device indicates the load detected by the load detector, when the load detected by the load detector exceeds a second reference load smaller than a first reference load.

13. The dental apparatus as claimed in claim 12, wherein the lead information device changes the load indicating state with flashing and changing colors.

14. The dental apparatus as claimed in claim 1, further comprising a sound alarm for giving a sound when the load detected by the load detector exceeds a second reference load smaller than a first reference load.

15. The dental apparatus as claimed in claim 1, further comprising a rotation speed control device for controlling the driving device to gradually decrease a rotation speed of the cutting tool when the load detected by the load detector approaches a reference load.

16. The dental apparatus as claimed in claim 1, further comprising an audible direction indicator for indicating driven direction of the cutting tool audibly.

17. The dental apparatus as claimed in claim 1, wherein the load information device is provided with a display portion placed on a handpiece in which the driving device and the load detector are disposed.

18. The dental apparatus as claimed in claim 1, further comprising a root canal length measuring device and plural segments arranged two-dimensionally in a first direction and in a second direction nearly perpendicular to the first direction,
   wherein the load information device indicates the root canal length measured by the root canal length measuring device in accordance with the positions of at least one of displayed segments among the plural segments arranged in the first direction, and
   wherein the load information device indicates the load detected by the load detector in accordance with the width of displayed segments among the plural segments arranged in the second direction.

19. The dental apparatus as claimed in claim 1, further comprising
   a root canal length measuring device for measuring a root canal length; and
   a control device for controlling the driving device so that a driving force of the cutting tool changes depending on a measurement value of the root canal length measured by the root canal length measuring device, wherein the control device controls the driving device to perform one of stopping a rotation of the cutting tool; reversing the rotation thereof; decreasing a speed of the rotation thereof; and repeating forward and backward rotations thereof.

20. The dental apparatus as claimed in claim 19, wherein the control device includes a rotation control device for controlling the driving device so that the rotation of the cutting tool changes depending on the measurement value of the root canal length measured by the root canal length measuring device.

21. The dental apparatus as claimed in claim 20, wherein the rotation control device controls the driving device so that the rotation speed of the cutting tool changes from a reference rotation speed to a preset rotation speed depending on the measurement value of the root canal length measured by the root canal length measuring device.

22. The dental apparatus as claimed in claim 21, further comprising a setting device for setting the reference rotation speed and the preset rotation speed.

23. The dental apparatus as claimed in claim 20, wherein the rotation control device controls the driving device so that the rotation speed of the cutting tool changes from a reference rotation speed at a preset reduction rate depending on the measurement value of the root canal length measured by the root canal length measuring device.

24. The dental apparatus as claimed in claim 23, further comprising a setting device for setting the reference rotation speed and the reduction rate.

25. The dental apparatus as claimed in claim 1, further comprising a visible direction indicator for indicating driver direction at the cutting tool visually.

* * * * *